United States Patent
Clausen et al.

(10) Patent No.: US 9,427,338 B2
(45) Date of Patent: Aug. 30, 2016

(54) METATARSAL JOINT SHAPE FOR PROSTHETIC FOOT AND CONTROL MECHANISM AND SYSTEM FOR SAME

(71) Applicant: Össur hf, Reykjavik (IS)

(72) Inventors: Arinbjörn Viggo Clausen, Reykjavik (IS); Lárus Gunnsteinsson, Reykjavik (IS)

(73) Assignee: Össur hf, Reykjavik (IS)

( * ) Notice: Subject to any disclaimer, the term of this patent is extended or adjusted under 35 U.S.C. 154(b) by 0 days.

(21) Appl. No.: 14/067,606

(22) Filed: Oct. 30, 2013

(65) Prior Publication Data

US 2014/0058531 A1    Feb. 27, 2014

Related U.S. Application Data

(63) Continuation of application No. 13/032,495, filed on Feb. 22, 2011, now Pat. No. 8,574,313.

(60) Provisional application No. 61/307,267, filed on Feb. 23, 2010.

(51) Int. Cl.
*A61F 2/66* (2006.01)
*A61F 2/68* (2006.01)
*A61F 2/50* (2006.01)

(52) U.S. Cl.
CPC .............. *A61F 2/66* (2013.01); *A61F 2/6607* (2013.01); *A61F 2002/5056* (2013.01); *A61F 2002/665* (2013.01); *A61F 2002/6635* (2013.01); *A61F 2002/6678* (2013.01)

(58) Field of Classification Search
CPC ............. A61F 2/66; A61F 2002/6635; A61F 2002/665; A61F 2002/6657
USPC ...................................... 623/55–56
See application file for complete search history.

(56) References Cited

U.S. PATENT DOCUMENTS

| | | | |
|---|---|---|---|
| 35,686 A | 6/1862 | Jewett | |
| 53,931 A | 4/1866 | Weston | |

(Continued)

FOREIGN PATENT DOCUMENTS

| | | |
|---|---|---|
| DE | 817186 | 10/1951 |
| DE | 834884 | 3/1952 |

(Continued)

OTHER PUBLICATIONS

American Prosthetic Components, Inc. DuroFlex™ product shown in brochure (2 pages) and at http://www.apcomponents.com/NonMembers/DuroFlex.asp, available more than one year before Feb. 23, 2010.

(Continued)

*Primary Examiner* — Jacqueline Woznicki
(74) *Attorney, Agent, or Firm* — Knobbe, Martens, Olson & Bear, LLP

(57) ABSTRACT

A prosthetic foot can include a plate-like foot member extending along a longitudinal axis between an anterior end generally corresponding to a toe portion of a foot to a posterior end, and a metatarsal hinge comprising an elongate groove extending between medial and lateral edges of the foot member. The elongate groove can intersect the longitudinal axis of the foot member, and can be positioned along the length of the foot member at a location generally corresponding to a metatarsal region of the foot. The metatarsal hinge can also comprise a plurality of elongate apertures that extend completely through the foot member, or a plurality of recessed channels that extend only partially through the foot member, or a combination thereof.

19 Claims, 7 Drawing Sheets

(56) References Cited

U.S. PATENT DOCUMENTS

| | | |
|---|---|---|
| 57,666 A | 9/1866 | Bly |
| 368,580 A | 8/1887 | Frees |
| 411,377 A | 9/1889 | Fairchild |
| 809,876 A | 1/1906 | Wilkins |
| 987,893 A | 3/1911 | Lawrence |
| 1,023,247 A | 4/1912 | Frees |
| 2,529,968 A | 11/1950 | Sartin |
| 2,573,347 A | 10/1951 | Mazzola |
| 2,619,652 A | 12/1952 | Vesper |
| 2,692,392 A | 10/1954 | Bennington et al. |
| 2,731,645 A | 1/1956 | Woodall |
| 3,551,914 A | 1/1971 | Woodall |
| 4,652,266 A | 3/1987 | Truesdell |
| 5,181,933 A | 1/1993 | Phillips |
| 5,219,365 A | 6/1993 | Sabolich |
| 5,376,133 A | 12/1994 | Gramnas |
| 5,549,711 A | 8/1996 | Bryant |
| 5,653,768 A | 8/1997 | Kania |
| 6,241,776 B1 | 6/2001 | Christensen |
| 6,402,790 B1 | 6/2002 | Celebi |
| 6,596,029 B1 | 7/2003 | Gramnas |
| 6,602,295 B1 | 8/2003 | Doddroe et al. |
| 6,712,860 B2 | 3/2004 | Rubie et al. |
| 6,764,522 B1 | 7/2004 | Cehn |
| 6,942,704 B2 | 9/2005 | Sulprizio |
| 7,341,603 B2 | 3/2008 | Christensen |
| 7,347,877 B2 | 3/2008 | Clausen et al. |
| 7,507,259 B2 | 3/2009 | Townsend et al. |
| 7,578,852 B2 | 8/2009 | Townsend et al. |
| 7,763,082 B1 | 7/2010 | Curtis |
| 7,766,974 B2 | 8/2010 | Curtis |
| 7,819,926 B1 | 10/2010 | Longino |
| 7,846,213 B2 | 12/2010 | Lecomte et al. |
| 7,998,221 B2 | 8/2011 | Lecomte et al. |
| 8,025,699 B2 | 9/2011 | Lecomte et al. |
| 8,246,695 B2 | 8/2012 | Mosler |
| 8,317,876 B2 | 11/2012 | Mosler |
| 8,574,313 B2 | 11/2013 | Clausen et al. |
| 8,764,850 B2 | 7/2014 | Hansen et al. |
| 2002/0143406 A1 | 10/2002 | Townsend et al. |
| 2004/0225376 A1 | 11/2004 | Townsend et al. |
| 2005/0038525 A1 | 2/2005 | Doddroe et al. |
| 2005/0049721 A1 | 3/2005 | Sulprizio |
| 2006/0015192 A1 | 1/2006 | Clausen et al. |
| 2007/0100466 A1 | 5/2007 | Allert |
| 2008/0281436 A1 | 11/2008 | Townsend et al. |
| 2008/0306612 A1 | 12/2008 | Mosler |
| 2009/0105845 A1 | 4/2009 | Curtis |
| 2009/0204229 A1 | 8/2009 | Mosler et al. |
| 2012/0010730 A1 | 1/2012 | Lecomte et al. |

FOREIGN PATENT DOCUMENTS

| | | |
|---|---|---|
| DE | 298 20 904 | 6/1999 |
| GB | 117547 | 8/1918 |
| GB | 120462 | 11/1918 |
| WO | WO 91/15171 | 10/1991 |
| WO | WO 2011/106328 A1 | 9/2011 |

OTHER PUBLICATIONS

International Search Report and Written Opinion for PCT Application No. PCT/US2011/025766 filed on Feb. 22, 2011, mailed Apr. 15, 2011.

Extended European Search Report and Search Opinion for Application No. 11747938.6 filed on Aug. 21, 2012, Mailed on Dec. 18, 2013.

International Preliminary Report on Patentability in corresponding International Patent Application No. PCT/US2011/025766, dated Aug. 28, 2012.

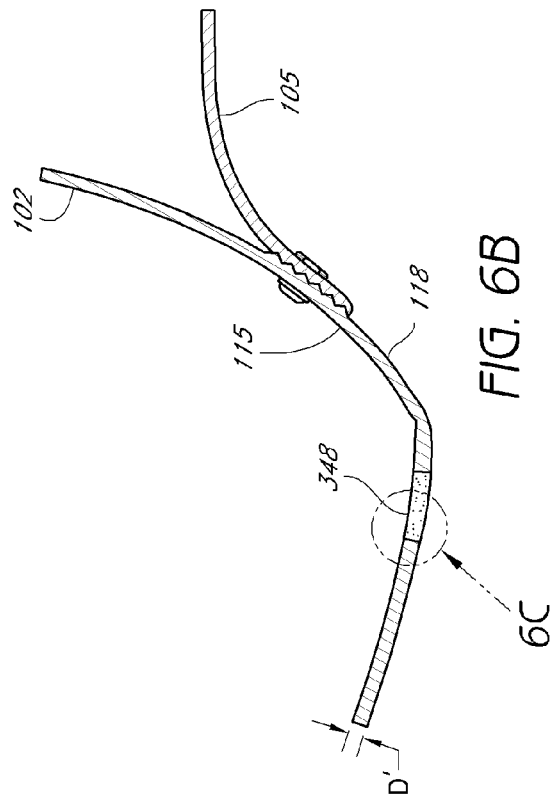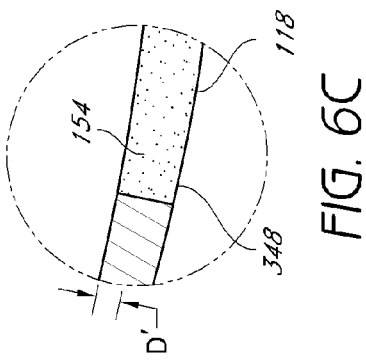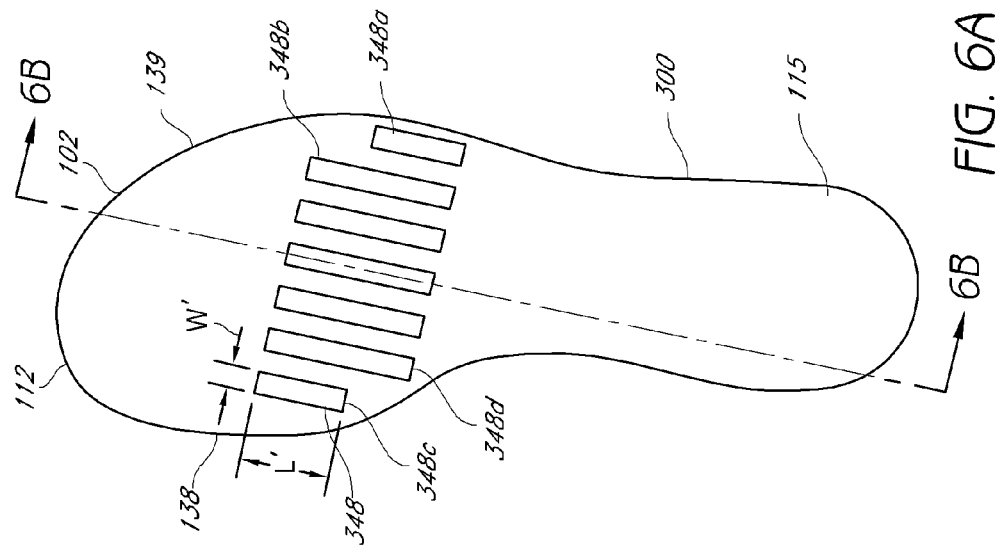

METATARSAL JOINT SHAPE FOR PROSTHETIC FOOT AND CONTROL MECHANISM AND SYSTEM FOR SAME

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation of U.S. application Ser. No. 13/032,495, filed Feb. 22, 2011, which claims priority under 35 U.S.C. §119(e) as a nonprovisional of U.S. Provisional App. No. 61/307,267, filed Feb. 23, 2010. This application is also related to U.S. patent application Ser. No. 12/509,055, filed Jul. 24, 2009, which is a continuation of U.S. patent application Ser. No. 10/987,940, filed Nov. 12, 2004, now issued as U.S. Pat. No. 7,846,213, which is a continuation-in-part of U.S. patent application Ser. No. 10/944,436, filed Sep. 17, 2004, now issued as U.S. Pat. No. 7,347,877, which claims priority to Provisional App. No. 60/575,142, filed May 28, 2004. The entire contents of each of these references is hereby incorporated by reference and should be considered a part of this specification.

BACKGROUND OF THE INVENTION

1. Field of the Invention

The present application relates in certain embodiments to prosthetic feet. In particular, the present application in certain embodiments relates to prosthetic feet with an articulatable metatarsal joint.

2. Description of the Related Art

Prosthetic feet are known in the art that are designed to replicate the natural function of human feet. These prosthetic feet may include components designed to mimic the natural function of ankles, heels and toes.

There is much difficulty in developing a prosthetic foot that mimics the natural function of human toes. The challenges may be even greater when trying to replicate a human toe that can account for other physical modifications of the prosthetic foot. For example, a user of a prosthetic foot may be able to modify its heel height by providing ankle adjustments. When the heel height is modified without adjusting other sections of the prosthetic foot (e.g., the toe region), this results in an unnatural position of the prosthetic foot that can create discomfort for the user or provide a less than optimal rollover performance during ambulation.

Despite advancements in prosthetics, there remains an on-going need to provide a prosthetic foot that properly captures the function of natural human toes by providing metatarsal functionality. The prosthetic foot should be capable of assisting in walking and providing balance, weight-bearing, thrust during gait and proper push-off patterns. The prosthetic foot should also be able to accommodate different types of heel-height adjustment.

SUMMARY OF THE CLAIMS

An improved prosthetic foot designed for providing metatarsal functionality is described. In one embodiment, the prosthetic foot includes a generally plate-like foot member that extends along a longitudinal axis between an anterior end, which can correspond to a toe portion, and a posterior end, which can correspond to a heel portion. The prosthetic foot can include an elongate groove that can extend across the width of the foot member between medial and lateral edges of the foot member so that the groove intersects the longitudinal axis of the foot member. In one embodiment, the elongate groove extends generally transverse to the longitudinal axis of the foot member from the lateral edge to the medial edge of the foot member. The position of the elongate groove generally corresponds to a metatarsal region of the foot.

In another embodiment, a prosthetic foot is provided comprising a plate-like foot member extending along a longitudinal axis between an anterior end generally corresponding to a toe portion of a foot to a posterior end. The foot member includes a top surface and a bottom surface opposite the top surface, wherein the bottom surface is configured to contact a support surface during ambulation of the prosthetic foot. The foot member can comprise at least one elongate groove defined on the top surface, wherein the elongated groove extends between medial and lateral edges of the foot member and intersects the longitudinal axis of the foot member. The elongated groove can be positioned along the length of the foot member at a location generally corresponding to a metatarsal region of a foot and can be configured to allow the anterior portion of the foot to controllably articulate relative to the posterior end of the foot. A filler material can be disposed in the elongate groove. The filler material can be configured to vary the rate and/or degree of articulation of the anterior portion of the foot relative to the posterior end of the foot.

BRIEF DESCRIPTION OF THE DRAWINGS

FIG. 6A illustrates a top view of a prosthetic foot having a metatarsal hinge formed of a plurality of apertures according to embodiments of the present application.

FIG. 6B illustrates a cross-sectional view of the prosthetic foot in FIG. 6A.

FIG. 6C illustrates an exploded view of a portion of the prosthetic foot in FIG. 6B having apertures filled with a filler material.

DETAILED DESCRIPTION OF THE EMBODIMENTS

Improved prosthetic feet are described that are capable of providing metatarsal functionality and mimicking the natural function of human feet. In particular, the prosthetic feet described herein include a metatarsal joint shape and control mechanism and system that can include a metatarsal hinge that provides metatarsal functionality. The prosthetic feet described herein advantageously assist in achieving the goals described above, including providing balance, improved push-off patterns and thrust during gait, even following heel-height adjustment.

Figure 1:
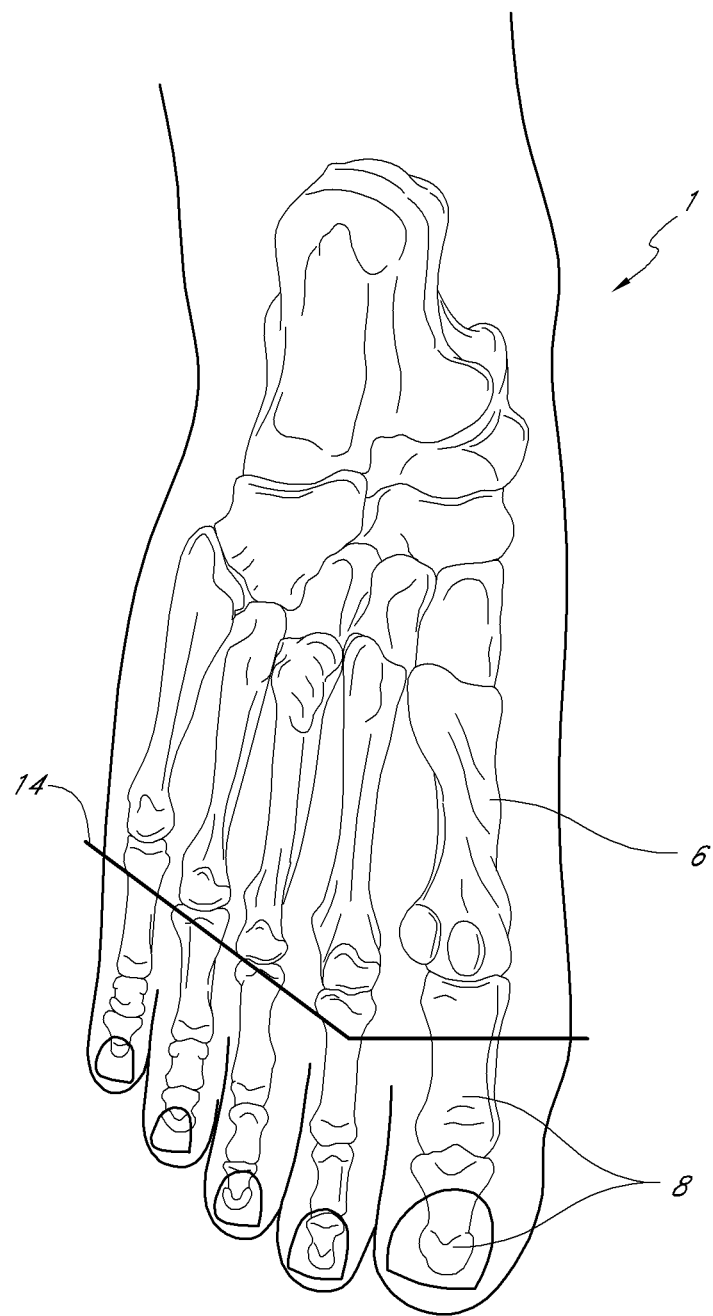
FIG. 1 illustrates an upper cross-sectional view of a human foot.

FIG. 1 illustrates an upper cross-sectional view of a human foot. The human foot 1 serves as a mechanical structure having bones, joints, muscles, tendons and ligaments. Bones in the human foot include metatarsal bones 6 and shorter phalanges 8 that form the toes. Metatarsophalangeal joints exist between the metatarsal bones 6 and phalanges 8. These joints assist in providing joint articulation of the phalanges 8 relative to the metatarsal bones 6, such as at the natural metatarsal angles 14 identified in FIG. 1, which allows the posterior or heel of the foot to be angled relative to the forefoot or toes of the foot. Said articulation allows the use of shoes of varying heel heights while providing support and balance.

In view of the challenges described above, the present application discloses an improved prosthetic foot having a metatarsal joint shape and control mechanism or system that advantageously mimics the metatarsal joints of a natural human foot, thereby providing metatarsal functionality and easily accommodating heel-height adjustment of the prosthetic foot. The metatarsal joint shape and control system can include one or more elongate gaps, channels, apertures, or grooves formed in the prosthetic foot (e.g., formed on a surface of a prosthetic foot plate). The position of the grooves generally corresponds to a metatarsal region of the foot. In some embodiments, the metatarsal region of the foot comprises approximately ¼ to ⅓ or more of the foot length from an anterior edge of the foot. In other embodiments, to find the metatarsal region, the length of the foot can be multiplied by 0.618, and this distance can be travelled from a posterior edge. The grooves can be open or filled with a resilient material, and can be used to provide the prosthetic foot with metatarsal functionality, allowing the prosthetic foot to articulate via the metatarsal joint.

Figure 2:
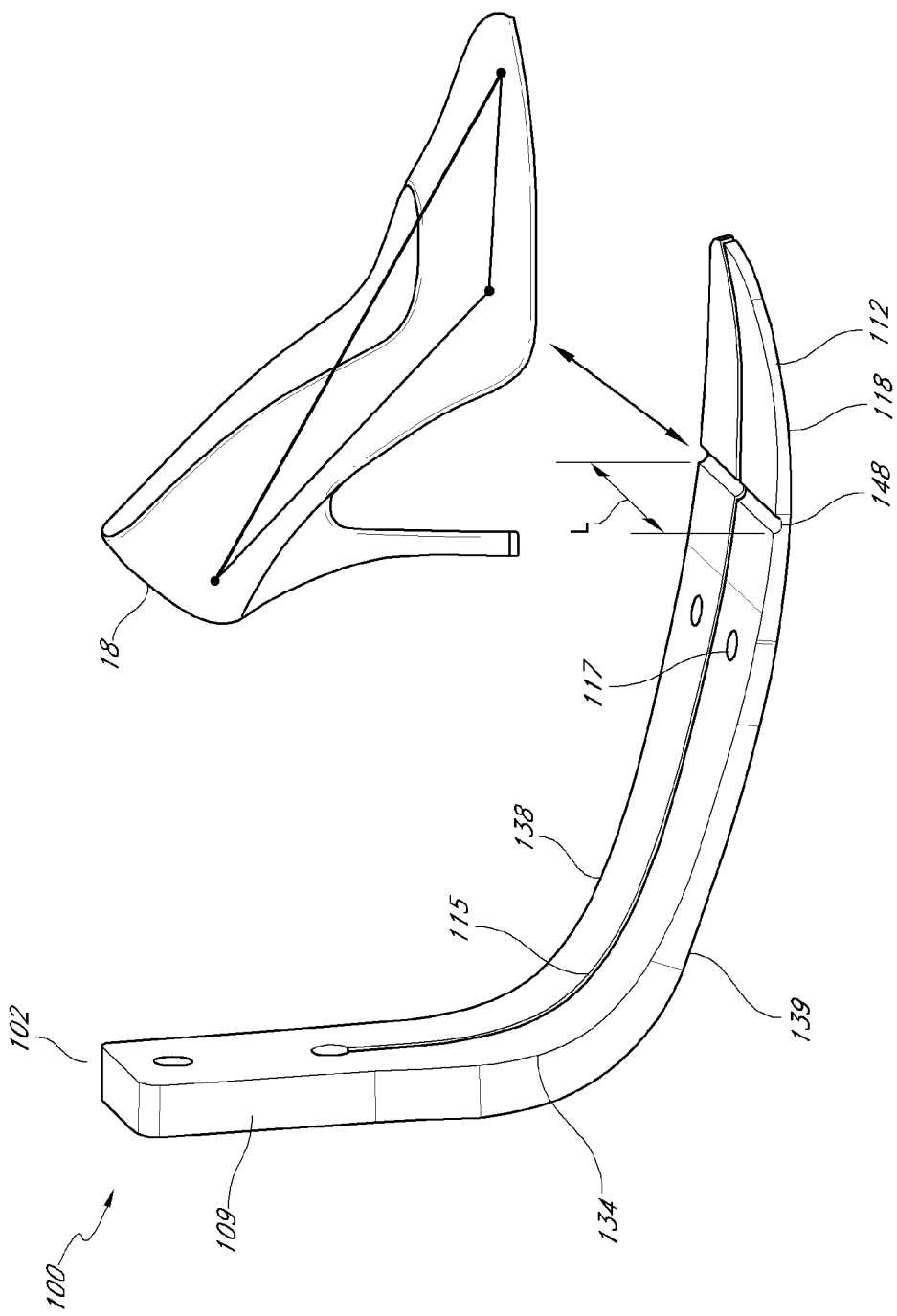
FIG. 2 illustrates a perspective view of a schematic of a prosthetic foot having a metatarsal hinge according to embodiments of the present application.

FIG. 2 illustrates a schematic of a prosthetic foot having a metatarsal hinge according to some embodiments of the present application. The prosthetic foot 100 can comprise a curved plate-like foot member 102 having a top surface 115 and bottom surface 118, as well as an upper portion 109 and a toe region 112. In one embodiment, at least a portion of the foot member 102 is generally planar. In one embodiment, a transverse cross-section of the foot member 102 can be generally rectangular. The foot member 102 can further include attachment holes 117 and a split 134 along its longitudinal axis that separates the plate-like member into two sections: a medial blade having medial edge 138 and a lateral blade having lateral edge 139. In other embodiments, the foot member 102 can have more than one longitudinal split or slot 134 defining two or more blades. In still another embodiment, the foot member 102 can be a single foot plate without a longitudinal split or slot. The foot member 102 can have a metatarsal hinge generally at the location of the metatarsal region in a natural human foot. In one embodiment, the metatarsal hinge can include a channel or groove 148 that intersects the longitudinal axis of the prosthetic foot. In one embodiment, the metatarsal hinge intersects the split or slot 134 of the foot member 102.

Figure 5:
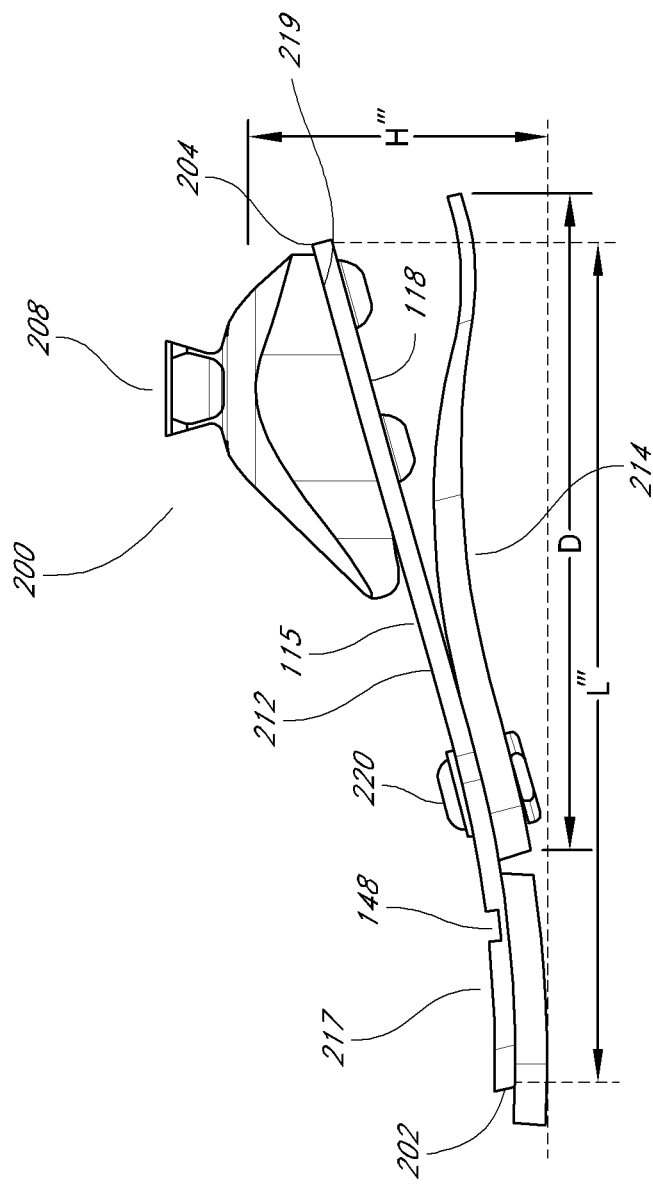
FIG. 5 illustrates a side view of a schematic of a prosthetic foot having a metatarsal hinge according to embodiments of the present application.

The foot member 102 of the prosthetic foot 100 can be a curved plate-like member having a posterior edge formed by the upper portion 109 and an anterior edge formed by the toe region 112. In shape, the plate-like foot member 102 includes a vertical upper portion 109 that slopes and curves downwardly before flattening out near the toe portion 112. At the toe portion 112, the foot member 102 slopes and curves upwardly and provides a slight raise from the ground at the anterior end. While the foot member 102 is shown on its own in FIG. 2, in some embodiments, the foot member can be operably connected to a heel member, as shown in FIGS. 5 and 6B.

In some embodiments, portions of the prosthetic foot (such as the foot member or heel member) can be constructed of a strong, resilient material that is capable of flexing in multiple directions, particularly during heel-strike through toe-off. The material can comprise multiple layers, or laminate. In some embodiments, the multiple layers or laminates when assembled form a monolithic foot member 102 of the prosthetic foot 100. Examples of possible materials for the prosthetic foot 100 include carbon, any polymer material, and any composite of polymer and fiber. The polymer can be thermoset or thermoplastic. In a composite, the fiber reinforcement can be any type of fiber or filament, such as carbon, glass or aramid. The fibers can be long and unidirectional, or they can be chopped and randomly oriented. Other filaments, such as Kevlar and nylon, can also be used to ensure lightweight and structurally dynamic characteristics.

The upper portion 109 of the foot member 102 can be attached to adapters and/or pylons for prosthetic limbs. While not shown in FIG. 2, attachment holes can be provided on the upper portion 109 to assist in attaching these additional components. Other than or in addition to the attachment holes that can be provided on the upper portion 109 of the prosthesis, attachment holes 117 can also be provided on other sections of the prosthetic foot, such as below the upper portion 109 closer to the anterior end of the foot. These attachment holes 117 can be used to affix the plate-like member to other members (e.g., a lower, plate-like heel member) by using mechanical screws, fasteners or bolts. An example of a prosthetic foot having an upper member attached to a lower member by use of attachment holes is shown in FIG. 5 and discussed further below. However, other suitable mechanisms can be used to attach the plate-like member to other members (e.g., adapter, heel plate, etc.). For example various adhesives may also be used to affix the plate-like member to other members.

The split 134 is located along the longitudinal axis of the foot member 102 and can help provide desirable roll-over properties. The split 134 is of a length that is between approximately ⅕ and ⅘ of the longitudinal length of the foot member 102, can begin at a distance that is between approximately ⅕ and ⅘ of the distance away from the posterior end of the foot member, and can extend to the distal edge of the foot member (i.e., to the edge of the toe region of the foot member). The split 134 separates portions of the foot member 102 into a medial blade having medial edge 138 and a lateral blade having lateral edge 139. While in FIG. 2, the medial blade and the lateral blade have equivalent widths, in other embodiments, the split 134 can form blades of unequal width. In addition, while the split 134 is entirely straight along a longitudinal axis of the foot member 102, in other embodiments, the split 134 has a straight portion followed by a curved portion that curves either in a lateral or medial direction toward the distal end of the foot member. In yet another embodiment, the split 134 can have a curved shape without any straight portions.

As shown in FIG. 2, the foot member 102 of the prosthetic foot 100 includes a metatarsal hinge comprising a gap, channel or groove 148 that can extend across the width of the foot member between medial and lateral edges of the foot member. In the illustrated embodiment, the groove 148 is formed as a recessed portion in the top surface 115 of the foot member 102. However, while the groove 148 is illustrated on a top surface 115 of the foot member 102, in other embodiments, the groove can be located on a bottom surface 118 of the foot member 102, or in between a top surface and bottom surface. In some embodiments, the groove 148 extends completely across the prosthetic foot, from one part of the medial edge to one part of the lateral edge, while in other embodiments the groove 148 extends across only a portion of the prosthetic foot. The groove 148 can intersect the longitudinal axis of the foot member 102. In some embodiments, the groove 148 can be generally transverse to the longitudinal axis of the foot member 102, and even perpendicular to the longitudinal axis, as shown in FIG. 2. In other embodiments, the groove 148 intersects the longitudinal axis of the foot member 102 at an angle other than 90 degrees, such as between 20 and 80 degrees. The prosthetic foot 100 comprising the groove 148 can be formed by special layup sequencing, where the groove 148 is defined by one or more layers, but fewer than all layers, that make up the foot member 102 of the prosthetic foot 100, or by cutting the groove through material layers of the foot member 102 of the prosthetic foot 100 after said layers have been laid.

Such techniques can be used to position the elongate groove 148 generally near or around the metatarsal region of the foot. In some embodiments, the metatarsal region or "toe section" of the foot can extend a length (either planar or curvilinear depending on the shape of the region) between about 0.5 cm and 20 cm, as measured from an anterior end (e.g., anterior edge) of the foot to the groove 148. One skilled in the art will appreciate that the length of the toe section is not limited to these lengths, and that the length can be determined in proportion to the length of the prosthetic foot. Providing a suitable length of the metatarsal region advantageously provides an effective toe length that helps to accommodate various stride lengths. With the groove 148 positioned generally near or around the metatarsal region, the prosthetic foot 100 is capable of flexing and comfortably accommodating heel height adjustments.

In one embodiment, the groove 148 can include sidewalls 216 that help to form the particular shape of the groove within the foot member 102. In some embodiments, the groove 148 includes sidewalls 216 that are straight, curved, or tapered. In some embodiments, the sidewalls 216 include "teeth" formed by elevations and depressions that can further help to enclose deposited filler material. From a cross-sectional view, the groove can be curved (e.g., generally circular), u-shaped, v-shaped, square-shaped, or any other suitable shape. For example, as illustrated in FIGS. 3A-4B, which show cross-sectional views of groove 148, the groove 148 can be shaped like a valley, having its narrowest point in its center or bottom most point.

The groove 148 can further take on various dimensions. In some embodiments, the depth D of the groove can be between 1/20 and 9/10 of the cross-sectional thickness of a section of the foot member or alternatively, the average height of the foot member itself. In other embodiments, the average width W of the groove (e.g., the distance from one sidewall of the groove to another sidewall) can be between 5 mm and 20 mm, more preferably between 5 mm and 10 mm. In one embodiment, the depth of the groove 148 can vary along the length L of the groove (illustrated in FIG. 2). For example, the depth D of the groove 148 can increase toward the medial edge of the foot member. The medial side of the foot member would thus be more flexible than the lateral side of the foot member, and thus, the groove helps to direct rollover of the foot member in the medial direction. Alternatively, the depth of the groove 148 can increase toward the lateral edge of the foot member. The lateral side of the foot member would thus be more flexible than the lateral side of the foot member, and thus, the groove helps to direct rollover of the foot member in the lateral direction. In addition, in some embodiments, the width W of the groove 148 can vary along the length L (e.g., it can increase in either a medial or lateral direction) of the groove to assist in directing rollover toward a medial or lateral edge of the foot member. One skilled in the art will appreciate, however, that the dimensions of the groove are not so limited, and that other dimensions are also possible, as the measurements of the groove can be determined in proportion to the type and/or thickness of a corresponding prosthetic foot. Advantageously, the groove 148 can help accommodate heel-height adjustment, such as would occur if the user wore a high-heel shoe 18 as shown in FIG. 2.

While the metatarsal hinge in FIG. 2 is illustrated as a single straight groove 148 that intersects the longitudinal axis of the foot member 102 in a generally transverse manner, in other embodiments, the metatarsal hinge can be formed of more than one groove. The one or more grooves can intersect the longitudinal axis of the foot member 102 of the prosthetic foot 100 at various angles, including along the natural metatarsal angles 14 of the human foot, as shown in FIG. 1. In some embodiments, the one or more grooves can include one or more portions that are transverse to the longitudinal axis, as well as one or more other portions that are slanted or placed at an angle from the portions that are transverse from the longitudinal axis. In some embodiments, relative to a segment of the foot member that is perpendicular to the longitudinal axis, the one or more grooves can have one or more portions that are at a slanted angle between about 0 and 85 degrees, more preferably between 0 and 45 degrees, to provide for metatarsal functionality. In one embodiment, the one or more grooves can have one or more portions that are at a slanted angle between about 0 and 20 degrees relative to a line perpendicular to the longitudinal axis (e.g., slanted at an angle of 90 to 110 degrees relative to the longitudinal axis).

While the groove 148 shown in FIG. 2 is formed on a top surface 115 of the curved plate-like foot member 102 of the prosthetic foot 100 (e.g., where the top surface 115 is a surface opposite the bottom surface 118 that can operatively contact a support surface, such as a floor, during ambulation), in some embodiments, the groove 148 can be formed on a bottom-surface 118 near the toe section. In other embodiments, an opening can be formed mid-way between a top-surface 115 and bottom-surface 118 near the toe section, such that the opening is only exposed on the side of the prosthetic foot. In still another embodiment, one or more grooves 148 can be formed on both the top and bottom surfaces of the foot member 102 of the prosthetic foot 100. Regardless of whether the opening or groove 148 is formed on a top surface, a bottom surface, or mid-way between a top surface and bottom surface of the curved plate-like foot member 102 of the prosthetic foot 100, the groove 148 can serve as an articulatable metatarsal joint that can remain open or be filled with a filler material, as discussed below. Furthermore, regardless of where the groove 148 is formed, the curved plate-like foot member 102 of the prosthetic foot 100 can still comprise a single piece whose body extends from a proximal edge to a distal edge.

While in some embodiments, the groove 148 can be left open (as shown in FIG. 2), in other embodiments, the groove 148 can be filled with a filler material 154. In some embodiments, the filler material can comprise a liquid, gel or solid (e.g., a solid insert insertable in the groove 148). In some embodiments, the filler material can comprise one or more polymers alone or in combination, such as polyurethane or silicone, as well as various other thermoplastic and thermosetting materials. Preferably, the filler material comprises a viscoelastic material comprising one or more types of synthetic polymers or elastomers, such as a gummy-material. Suitable elastomers can include, but are not limited to, materials under the trade names of Silly Putty, Sorbothane, Implus or Noene. In some embodiments, one or more grooves 148 can be filled with a combination of various materials as described above. In some embodiments, the filler material can be introduced into the groove 148 in liquid form prior to hardening upon placement in the groove 148. The various materials that can be inserted into the groove 148 can be resilient, and in some embodiments, can have a stiffness that differs from the other material of the prosthetic foot 100.

By adding the filler material 154 to the groove 148, a number of advantages can be achieved, including providing an adjustable stiffness or spring constant at or near the metatarsal region of the foot member, as well as enhanced resistance to deflection. For example, in one embodiment in which a high-heel adjustment is made, it may be desirable to provide no filler material, or a filler material 154 that provides great flexibility. If a filler material 154 is provided, upon removal of the high-heel adjustment, the material is resilient such that is can return to an original, unstressed state. In addition, in embodiments in which the foot member is formed of multiple layers, the filler material can help prevent layers from loosening and separating, thereby helping to keep the layers in place.

Forming a groove 148 near the toe section of the foot member 102 of the prosthetic foot 100 (with or without filler material) provides the prosthetic foot with an articulatable metatarsal hinge that is capable of flexing and adjusting at the natural metatarsal angles of the foot. By providing the metatarsal hinge, the prosthetic foot 100 is capable of comfortably articulating and flexing in various positions before, during and after heel-height adjustment. In some embodiments, adding an elastic filler material in the groove 148 advantageously helps to further control the extent of articulation by the metatarsal hinge. The elastic filler material, which can vary in stiffness depending on the material used, can help to provide a controlled return of the prosthetic foot to its normal position following heel height adjustment.

Figure 4A:
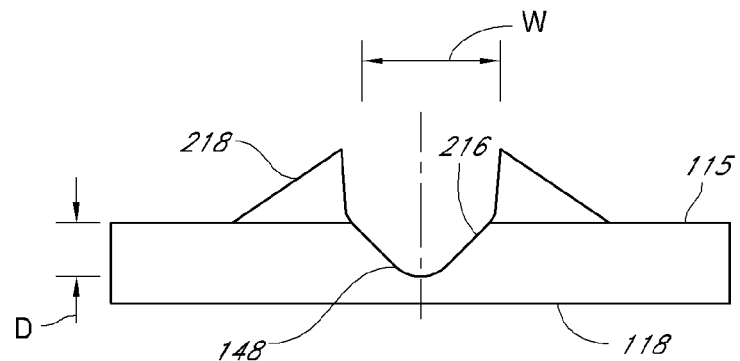
FIG. 4A illustrates a cross-sectional view of a metatarsal hinge comprised of an unfilled groove having raised side supports according to embodiments of the present application.
Figure 4B:
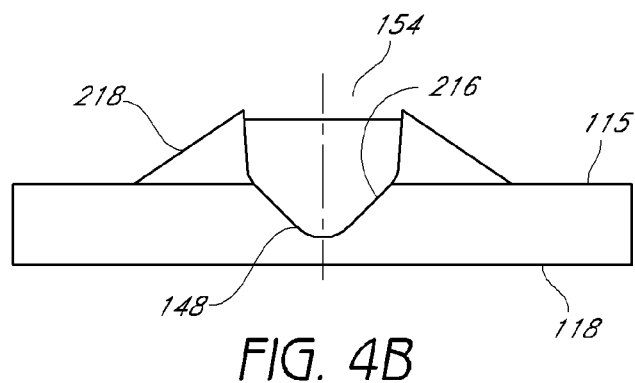
FIG. 4B illustrates a cross-sectional view of the groove of FIG. 4A filled with a filler material according to embodiments of the present application.

In some embodiments, a housing member (not shown) is provided that can enclose the deposited filler material. The housing member can include sidewalls that enhance the function of the filler material. For example, in some embodiments, the housing provides a constant volume for the filler material. In addition, the sidewalls of the housing can provide constraints for the movement of the filler material (e.g., floating liquid material) that can be contained in the housing. In some embodiments, the housing member can be formed with the groove 148 (e.g., as a lining member) that receives the filler material. In another embodiment, the housing can have generally the same cross-sectional shape as the groove 148. An optional cap or lining layer can be provided over the filler material to enclose the filler material once it is deposited in the prosthetic foot. In other embodiments, the housing member can accompany and surround the filler material (e.g., as a membrane) such that both can be inserted into and packed into the groove 148 simultaneously. Alternatively, or in addition to the housing member, the metatarsal hinge can include raised side supports 218, as shown in FIGS. 4A and 4B.

In some embodiments, the filler material 154 can be removable and replaceable after being deposited in the groove 148. For example, in some embodiments, the filler material 154 can be kept in one or more membranes as a package or insert that can be readily inserted and subsequently removed from the groove 148. By providing packages or inserts of filler material that are removable and/or replaceable, this advantageously allows the prosthetic foot to be used with an even greater array of heel-height adjustments.

Figure 3A:
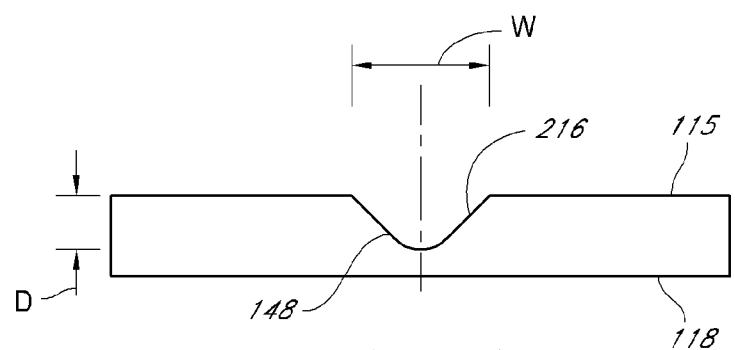
FIG. 3A illustrates a cross-sectional view of a metatarsal hinge comprised of an unfilled groove according to embodiments of the present application.

FIG. 3A illustrates a cross-sectional view of a metatarsal hinge comprised of an unfilled groove according to embodiments of the present application. The unfilled groove 148 has curved sidewalls 216 that form a valley. As shown in FIG. 3A, the curved sidewalls 216 of the groove 148 are positioned below the top surface 115 of the foot member. The unfilled groove 148 can be formed near a toe section of a prosthetic foot and can help provide articulatable metatarsal function.

Figure 3B:
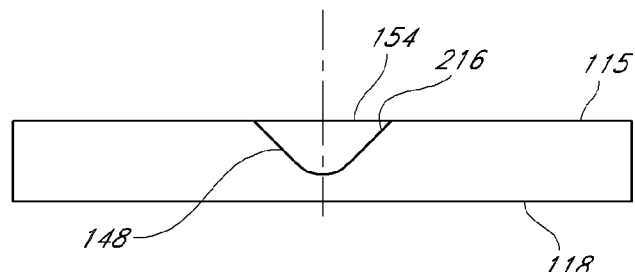
FIG. 3B illustrates a cross-sectional view of the groove in FIG. 3A filled with a filler material according to embodiments of the present application.

FIG. 3B illustrates a cross-sectional view of the groove of FIG. 3A filled with a filler material. The filler material 154 can be selected from any of the filler material described above, and preferably comprises a viscoelastic liquid. As shown in FIG. 3B, the filler material can occupy the entire volume of the groove 148. However, in other embodiments, the filler material need only occupy a portion of the volume of the groove 148 (e.g., a quarter of the volume or half of the volume). In some embodiments, the filler material 154 advantageously helps to provide greater control over the flexing and articulation of the metatarsal joint mechanism.

FIG. 4A illustrates a schematic of a metatarsal hinge in the form of a groove 148 having raised side supports 218 according to some embodiments of the present application. In contrast to the sidewalls 216 that are positioned below the top surface 115 of the plate-like foot member, the raised side supports 218 extend from and above the top surface 115 of the plate-like foot member. While the raised side supports 218 can be triangularly-shaped wings, as shown in FIG. 4A, in other embodiments, the raised side supports 218 can take on other shapes and forms (e.g., they can be square or rectangular). In some embodiments, the raised side supports 218 comprise raised flanges that extend from the top surface of the grooves. In some embodiments, the raised side supports 218 extend at a height of between about 1 mm and 50 mm above the upper surface of the plate-like member. The raised side supports 218 advantageously provide an increased volume for receiving filler material in the groove 148, thereby allowing for even greater metatarsal functionality. In some embodiments, the raised side supports 218 extend along an entire length L of the groove (shown in FIG. 2), while in other embodiments, the raised side supports 218 extend only along a portion of the entire length L of the groove. For example, the raised side supports 218 can be positioned along a portion of the groove that is less than the width of the foot. In some embodiments, the raised side supports 218 can be formed continuously along at least a portion of the length of the groove, while in other embodiments, the raised side supports 218 can be staggered along at least a portion of the length of the groove.

In some embodiments, the raised side supports 218 are formed with the plate-like foot member 102 of the prosthetic foot 100 (e.g., by a metal injection molding). In other embodiments, the raised side supports 218 are formed separately from the foot member 102 of the prosthetic foot 100 and subsequently attached (e.g., by an adhesive or by a screw). One skilled in the art will appreciate that the housing and raised side supports 218 are optional, and it is possible to provide a filler material that is flush against the sidewalls of the groove 148.

Preferably the raised side supports are composed of a resilient and compressible material capable of some flexing which does not interfere with the user when wearing various shoes (e.g., high heels). In some embodiments, the raised side supports are composed of various polymers, such as EVA or polyurethane. Various elastomers such as those described with respect to the filler material can also be used. In some embodiments, the raised side supports are composed of low compressible or non-compressible materials, including polymers of epoxides, polyamides, polycarbonates, polyimides, polyetherimides, and silicone polymers.

FIG. 4B illustrates a cross-sectional view of the groove of FIG. 4A filled with a filler material according to embodiments of the present application. With the addition of the raised side supports 218, filler material 154 can optionally be deposited in the groove 148 to a height above the top surface of the groove 148 (e.g., above the top surface 115 of the foot member), as shown in FIG. 4B. In some embodiments, the additional filler material 154 deposited in the groove 148 above the top surfaces of the grooves 148 provides additional resilience and control over the flexibility and articulation of the metatarsal hinge.

The metatarsal hinge described above can be used with a variety of other prosthetic feet in addition to those described above. FIG. 5 shows one such example of an alternative prosthetic foot 200 for which the metatarsal hinge can be used with. The prosthetic foot 200 includes an upper element 212 having a forefoot portion 217 and a posterior portion 219, a lower element 214, an adapter element 208 and groove 148 formed in a top surface 118 of the upper element 212. In some embodiments, the upper element 212 comprises a foot plate, while the lower element 214 comprises a heel plate that is operably attached to the foot plate.

The upper element 212 includes the forefoot portion 217, the posterior portion 219, and a curved portion therebetween. In another embodiment, the upper element 212 can be generally planar. In some embodiments, a cross-sectional area of the upper element 212 can be generally rectangular. The forefoot portion 217 comprises a metatarsal region or toe section. In one embodiment, at least a portion of the forefoot portion 217 can be generally horizontal and extend from an anterior end 202, or forward edge, of the prosthetic foot 200 toward a posterior end 204, or rearward edge, of prosthetic foot 200. The forefoot portion 217 can curve upward via a curvilinear portion and transition to the posterior portion 219 of the upper element 212. A top surface 115 of the posterior portion 219 of the upper element 212 can be operably connected to an adapter element 208 (e.g., via fasteners).

An unfilled groove 148 is located within or proximate to a forefoot portion 217 of the upper element 212 of the prosthetic foot 200. The unfilled groove 148 serves as an articulatable metatarsal hinge. While not shown, in another embodiment, a filler material can be provided in the groove 148 of the upper element 212 of the prosthetic foot 200, as discussed above.

As shown in FIG. 5, a bottom surface 118 of the upper element 212 can be disposed above the lower element 214. In one embodiment, at least a portion of the lower element 214 can be disposed adjacent and in contact with at least a portion of the bottom surface 118 of the upper element 212. In one embodiment, the upper element 212 can be operably coupled (e.g., via fasteners 220) to the lower element 214. The lower element 214 can serve as a heel member. In another embodiment, instead of the upper element 212 and lower element 214 being two separate pieces attached to one another, the upper element 212 and the lower element 214 can be one piece. The prosthetic foot 200 can interact with the ambulation, or walking, surface, via contact with lower element 214 which serves as a heel member. In still another embodiment (not shown), the upper and lower elements can be generally parallel along at least a portion of their lengths and separated at least in part by a compressible material. In one embodiment, the lower element can be disposed below and spaced apart from the upper element along its entire length.

Figure 6D:
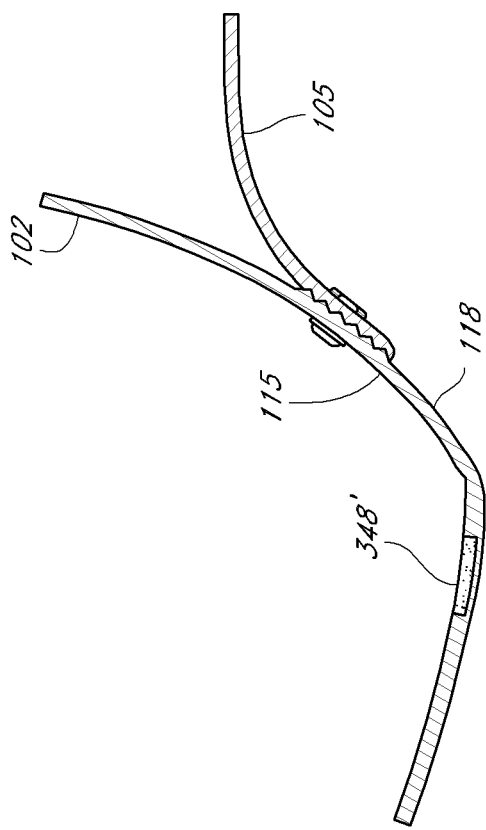
FIG. 6D illustrates a cross-sectional view of an alternate embodiment of a prosthetic foot having a metatarsal hinge formed of a plurality of recessed grooves according to embodiments of the present application.

FIG. 6A illustrates a top view of a prosthetic foot having a metatarsal hinge formed of a plurality of apertures according to embodiments of the present application. FIG. 6B illustrates a cross-sectional view of the prosthetic foot in FIG. 6A with the plurality of apertures unfilled with a filler material, while FIG. 6C illustrates an exploded view of a portion of the prosthetic foot in FIG. 6B having apertures filled with a filler material. FIG. 6D illustrates a cross-sectional view of an alternate embodiment of a prosthetic foot having a metatarsal hinge formed of a plurality of recessed grooves according to embodiments of the present application.

FIG. 6A illustrates a top view of a prosthetic foot having a metatarsal hinge formed of a plurality of elongate apertures that extend completely through the prosthetic foot. The prosthetic foot 300 can comprise a curved plate-like foot member 102 having a top surface 115, a bottom surface 118, a medial edge 138, a lateral edge 139 and a toe region 112. As shown in FIG. 6B, the curved plate-like foot member 102 can be operably attached to a heel member 105, such that at least a portion of the bottom surface 118 of the foot member 102 is in contact with a top surface of the heel member 105. A plurality of apertures 348 can extend through the top surface 115 of the foot member 102. In the illustrated embodiment in FIG. 6A, the plurality of apertures 348 extend completely through the foot member 102 of the prosthetic foot 300, from a top surface 115 to a bottom surface 118 (identified in FIG. 6B). However, in other embodiments, the apertures or grooves can extend only partly through the foot member 102 of the prosthetic foot 300, such that the plurality of apertures resemble recessed channels or grooves, as shown in FIG. 6D. As shown in FIG. 6A, the apertures 348 can have sides represented by a width W' and a length L'. At least some of sides of the apertures 348 can be in parallel with one another. Providing apertures 348 advantageously help the prosthetic foot to be more flexible, and allows the foot to mimic more accurately the biomechanical function of the anatomical foot.

Figure 6E:
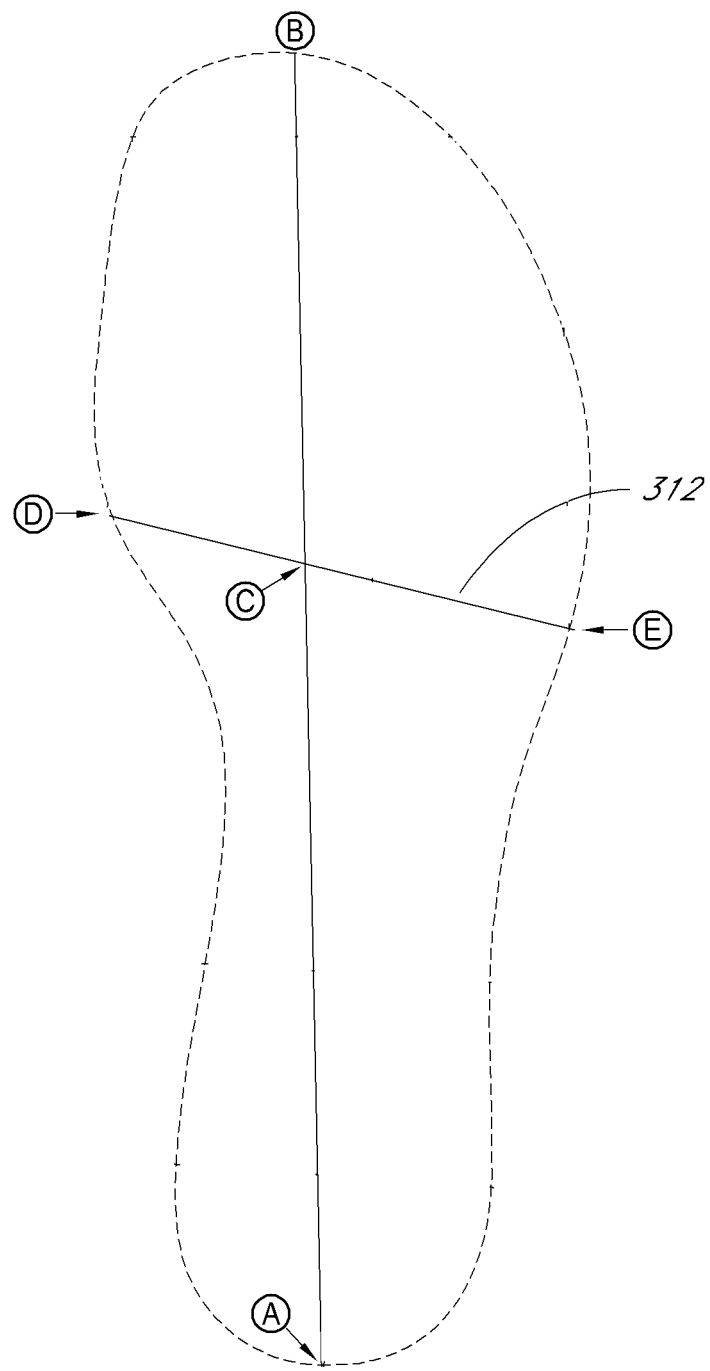
FIG. 6E illustrates a top view of a contour of a foot including metatarsal point C.

In some embodiments, the plurality of elongate apertures 348 can be formed generally along a line that intersects a longitudinal axis of the foot. In some embodiments, the plurality of elongate apertures 348 can be formed generally along a line that is perpendicular to a longitudinal axis of the foot, while in other embodiments, the elongate apertures 348 can be formed generally along a line that while not perpendicular, is askew, to a longitudinal axis of the foot. For example, as shown in FIG. 6E, the plurality of elongate apertures 348 can be formed along the line 312 from point D across metatarsal point C to point E, which is at an angle of approximately 110° relative to the longitudinal axis defined by points A and B.

As shown in FIG. 6A, the plurality of apertures 348 can be formed across a width of the prosthetic foot. In some embodiments, the plurality of apertures 348 can each be of similar dimensions (e.g., same width W' and length L'), while in other embodiments, some apertures may be of a different dimension than others (e.g., have a different width W' and/or length L'). For example, as shown in FIG. 6A, apertures 348a and 348c have a smaller length L' than apertures 348b and 348d. In addition, while the apertures 348 are illustrated as rectangular in shape, apertures of other shapes, such as circular, oval, square or triangular, can also be formed. For example, the prosthetic foot can comprise a metatarsal hinge formed of a series of circular apertures formed through the prosthetic foot to provide metatarsal functionality. In addition, a combination of apertures of various shapes and sizes can also be provided. In some embodiments, the apertures can be formed by performing a watercut on the carbon layers (e.g., using a water jet cutter), either before molding or after a layer-up process.

In other embodiments, rather than providing a plurality of apertures 348 that extend completely through the foot member 102 from a top surface 115 to a bottom surface 118 visible in FIG. 6B, the prosthetic foot 300 can comprise a plurality of recessed grooves or channels 348' that do not extend completely through the foot member 102 (as illustrated in FIG. 6D). The recessed grooves 348' can be formed either on a top surface 115 of a prosthetic foot, a bottom surface 118 of a prosthetic foot, or in between a top surface and bottom surface. In one embodiment, the recessed grooves 348' can assume the same shape (e.g., rectangular) and pattern across a width of the foot as the apertures 348 shown in FIG. 6A. The difference is that the recessed grooves 348' only extend through a portion of the height of the foot from the top surface 115 to a bottom surface 118 of the foot. In some embodiments, the recessed grooves 348' have a depth D' that is between about 1/10 to 3/4 of the height of the foot from a top surface to a bottom surface of the foot member 102. The depth of the recessed grooves 348' can be between about 0.05 mm and 6 mm, or between about 2 mm and 4 mm. In some embodiments, the foot member of the prosthetic foot 300 can include a combination of both apertures 348 that extend completely from a top surface 115 to a bottom surface 118 of the foot and recessed grooves 348' that extend only partially from the top surface 115 or bottom surface 118 of the foot.

In some embodiments, the plurality of recessed grooves can be formed by removing layers of material from sections of the prosthetic foot. For example, in some embodiments in which the foot member of the prosthetic foot is formed of multiple layers of carbon (e.g., about 40 layers), it is possible to remove a number of the layers (e.g., between 5 and 30 layers) to form recessed grooves in the foot member. Alternatively, the foot member of the prosthetic foot can be formed by performing a special layup sequencing, in which the recessed grooves are defined by one or more layers, but fewer than all layers, that make up the prosthetic foot 300.

In some embodiments, the apertures 348 or recessed grooves 348' can be filled with one or more filler materials. For example, as shown in the exploded view in FIG. 6C, the apertures 348 can be filled with a filler material 154. The filler material 154 can comprise any of the materials described above, including various liquids, gels or solids, or combinations thereof. In some embodiments, the filler material 154 comprises a gummy material or polyurethane. One or more filler materials (e.g., two, three or more) can be used to occupy at least a portion (if not all) of one or more apertures 348 or recessed grooves 348'. By providing a filler material 154, this advantageously helps to further control the extent of articulation by the metatarsal hinge formed by the plurality of apertures 348 and/or recessed grooves 348'. In addition, using the filler material 154 can help provide better rollover properties for the foot. And in embodiments in which the prosthetic foot is formed of layers of carbon fiber, which are subject to loosening or springing, the filler material 154 helps to hold the layers together and in place.

The filler material 154 can be provided in a housing member as discussed above that enhances the function of the filler material. In addition, the filler material 154 can be packaged or inserted in a membrane, such that in some embodiments, the filler material can be insertable and/or removable from the apertures 348 or recessed grooves 348'. In some embodiments, only a portion of the apertures 348 or recessed grooves 348' are filled with a filler material, while in other embodiments, all of the apertures 348 or recessed grooves 348' are filled with a filler material.

In addition to the prosthetic feet 100, 200 and 300 described above, the inventive articulatable metatarsal joint formed of a channel or groove, as described herein, can be used with various other feet having different or additional features as described above. For example, the metatarsal hinge can be used with the prosthetic feet described in U.S. patent application Ser. No. 07/029,947, filed on Mar. 26, 1987, now issued as U.S. Pat. No. 4,822,363 , U.S. patent application Ser. No. 07/293,824, filed on Jan. 5, 1989, now issued as U.S. Pat. No. 5,037,444 , U.S. patent application Ser. No. 07/337,374, filed on Apr. 13, 1989, now issued as U.S. Pat. No. 5,181,932 U.S. patent application Ser. No. 10/642,125, filed on Aug. 15, 2003 , and U.S. patent application Ser. No. 10/674,736, filed on Sep. 30, 2009 , all of which are incorporated by reference in their entireties.

Of course, the foregoing description is that of certain features, aspects and advantages of the present invention, to which various changes and modifications can be made without departing from the spirit and scope of the present invention. Moreover, the prosthetic foot need not feature all of the objects, advantages, features and aspects discussed above. Thus, for example, those skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed prosthetic foot. Thus, it is intended that the present invention cover the modifications and variations of this invention provided that they come within the scope of the appended claims or their equivalents.

What is claimed is:

1. A prosthetic foot comprising:
a monolithic plate-like foot member extending along a longitudinal axis between an anterior end corresponding to a toe portion of a foot and a posterior end, the foot member comprising a top surface, a bottom surface opposite the top surface, a split extending parallel to the longitudinal axis and at least partially separating the foot member into medial and lateral blades having unequal width, and a groove extending downward from the top surface and extending between medial and lateral edges of the foot member, wherein the groove comprises a first portion extending at a first transverse angle relative to the longitudinal axis of the foot member and a second portion extending at a second transverse angle relative to the longitudinal axis of the foot member, wherein the second transverse angle is different than the first transverse angle, wherein at least one of the first and second portions intersects the longitudinal axis of the foot member at an angle other than 90 degrees, and wherein the groove is positioned along the length of the foot member at a location generally corresponding to a metatarsal region of a natural human foot, the groove configured to allow an anterior portion of the foot to controllably articulate relative to a posterior portion of the foot.

2. The prosthetic foot of claim 1, wherein the at least one of the first and second portions of the groove intersects the longitudinal axis of the foot at an angle in the range of 20 degrees to 80 degrees.

3. The prosthetic foot of claim 1, wherein the groove is shaped such that a cross-sectional width continuously decreases from a top to a bottom of the elongate groove.

4. The prosthetic foot of claim 1, wherein the groove is V-shaped.

5. The prosthetic foot of claim 1, wherein the groove has a generally curved cross-sectional shape.

6. The prosthetic foot of claim 1, wherein a depth of the groove is between 1/20 and 9/10 of a cross-sectional thickness of the foot member.

7. The prosthetic foot of claim 1, further comprising a filling material disposed in the groove, the filling material configured to vary the resistance to deflection of the foot member at the location of the groove.

8. The prosthetic foot of claim 1, further comprising an adapter attached to the posterior end of the foot member.

9. A prosthetic foot comprising:
a monolithic plate-like foot member extending along a longitudinal axis between an anterior end corresponding to a toe portion of a foot and a posterior end, the foot member comprising a top surface and a bottom surface opposite the top surface;
a split extending parallel to the longitudinal axis and at least partially separating the foot member into medial and lateral blades having unequal width; and
a groove defined by the foot member and extending downward from the top surface and extending between medial and lateral edges of the foot member, wherein the groove comprises at least a first portion that extends at a non-perpendicular transverse angle relative to the longitudinal axis, wherein the groove comprises a second portion that extends at a transverse angle relative to the longitudinal axis that is different from the non-perpendicular transverse angle relative to the longitudinal axis of the first portion, and wherein the groove is positioned at a location generally corresponding to a metatarsal region of a natural human foot, the groove configured to allow an anterior portion of the foot to controllably articulate relative to a posterior portion of the foot,
wherein the foot member is formed of a plurality of layers of a resilient material and the groove is defined by one or more layers, but fewer than all of the plurality of layers of the foot member.

10. The prosthetic foot of claim 9, wherein the first portion of the groove extends at an angle between 0 and 85 degrees relative to a line extending transverse to the longitudinal axis of the foot member.

11. The prosthetic foot of claim 9, wherein the first portion of the groove extends at an angle between 0 and 45 degrees relative to a line extending transverse to the longitudinal axis of the foot member.

12. The prosthetic foot of claim 9, wherein the first portion of the groove extends at an angle between 0 and 20 degrees relative to a line extending transverse to the longitudinal axis of the foot member.

13. The prosthetic foot of claim 9, wherein the groove is shaped such that a cross-sectional width continuously decreases from a top to a bottom of the elongate groove.

14. The prosthetic foot of claim 9, wherein the groove is V-shaped.

15. The prosthetic foot of claim 9, wherein the groove has a generally curved cross-sectional shape.

16. The prosthetic foot of claim 9, wherein a depth of the groove is between 1/20 and 9/10 of a cross-sectional thickness of the foot member.

17. The prosthetic foot of claim 9, further comprising an adapter attached to the posterior end of the foot member.

18. The prosthetic foot of claim 9, further comprising a filling material disposed in the groove, the filling material configured to vary the resistance to deflection of the foot member at the location of the groove.

19. The prosthetic foot of claim 9, the groove further comprising a portion extending transverse to the longitudinal axis of the foot member.

* * * * *